US012801208B2

(12) United States Patent
Kim et al.

(10) Patent No.: US 12,801,208 B2
(45) Date of Patent: Nov. 17, 2026

(54) APPARATUS AND METHOD FOR DETERMINING A SITTING POSTURE

(71) Applicant: PUKYONG NATIONAL UNIVERSITY INDUSTRY-UNIVERSITY COOPERATION FOUNDATION, Busan (KR)

(72) Inventors: Jong Nam Kim, Busan (KR); Jae Eun Lee, Busan (KR); Young Bong Kim, Busan (KR)

(73) Assignee: PUKYONG NATIONAL UNIVERSITY INDUSTRY—UNIVERSITY COOPERATION FOUNDATION, Busan (KR)

( * ) Notice: Subject to any disclaimer, the term of this patent is extended or adjusted under 35 U.S.C. 154(b) by 241 days.

(21) Appl. No.: 18/685,034

(22) PCT Filed: Dec. 15, 2023

(86) PCT No.: PCT/KR2023/020756
§ 371 (c)(1),
(2) Date: Jan. 22, 2025

(87) PCT Pub. No.: WO2024/136335
PCT Pub. Date: Jun. 27, 2024

(65) Prior Publication Data

US 2025/0390163 A1 Dec. 25, 2025

(30) Foreign Application Priority Data

Dec. 22, 2022 (KR) ........................ 10-2022-0181962

(51) Int. Cl.
*G06F 3/01* (2006.01)
*A61B 5/00* (2006.01)
*A61B 5/11* (2006.01)

(52) U.S. Cl.
CPC ................ *G06F 3/011* (2013.01); *A61B 5/00* (2013.01); *A61B 5/11* (2013.01); *A61B 5/1116* (2013.01); *A61B 5/486* (2013.01); *A61B 5/746* (2013.01)

(58) Field of Classification Search
CPC ... G06F 3/011; A61B 5/00; A61B 5/11; A61B 5/1116; A61B 5/746; A61B 5/486
See application file for complete search history.

(56) References Cited

U.S. PATENT DOCUMENTS 12,515,571 B2 * 1/2026 Baudu .................. B60N 2/0244
12,530,954 B2 * 1/2026 Kwok ................ G08B 21/0446
(Continued)

FOREIGN PATENT DOCUMENTS

CN 115414031 A * 12/2022 ........... A61B 5/1075
KR 10-1847770 B1 4/2018
(Continued)

*Primary Examiner* — John A Tweel, Jr.
(74) *Attorney, Agent, or Firm* — NSIP Law

(57) ABSTRACT

A sitting posture determination device and a method thereof are proposed. The device includes a measurement data generation unit for generating measurement data composed of top portion measurement values and bottom portion measurement values for time points over time by receiving the top and bottom portion measurement values respectively input from top and bottom portion distance sensors, a correct posture determination unit for outputting a time point-specific top portion measurement value and bottom portion measurement value, which are out of a range preset for correct posture, by extracting the top and bottom portion measurement values from the measurement data and comparing the top and bottom portion measurement values with
(Continued)

the range preset for the correct posture, and a posture classification unit for selecting and outputting any one of classification values corresponding to postures preset according to the top and bottom portion measurement values at each time point.

7 Claims, 7 Drawing Sheets

(56) References Cited

U.S. PATENT DOCUMENTS

| | | | | |
|---|---|---|---|---|
| 2018/0365959 | A1 | 12/2018 | Hall et al. | |
| 2020/0405221 | A1* | 12/2020 | Kwak | A61B 5/4561 |
| 2024/0193981 | A1* | 6/2024 | Pearce | G06V 40/103 |
| 2025/0336517 | A1* | 10/2025 | Everard | G16H 40/67 |

FOREIGN PATENT DOCUMENTS

| | | | | | |
|---|---|---|---|---|---|
| KR | 20200001748 | A | * | 1/2020 | A61B 5/1116 |
| KR | 10-2232346 | B1 | | 3/2021 | |
| KR | 20220094634 | A | * | 7/2022 | A61B 5/486 |

* cited by examiner

APPARATUS AND METHOD FOR DETERMINING A SITTING POSTURE

CROSS REFERENCE TO RELATED APPLICATIONS

This application is a U.S. National Stage Application of International Application No. PCT/KR2023/020756, filed on Dec. 15, 2023, which claims the benefit under 35 USC 119(a) and 365(b) of Korean Patent Application No. 10-2022-0181962, filed on 22 Dec. 2022, in the Korean Intellectual Property Office, the entire disclosure of which is incorporated herein by reference for all purposes.

TECHNICAL FIELD

The present disclosure relates to a sitting posture determination device and method capable of determining a sitting posture according to distances between a monitor and a user, the distances being measured by using distance sensors.

BACKGROUND ART

In modern society, many tasks are performed through computers, so the number of people sitting in front of the computers for a long time is increasing. In a case where a person sits in front of a monitor, his or her posture may naturally become disturbed and the person takes slouched postures. When the person remains in such slouched posture for a long time, various physical symptoms such as poor eyesight, turtle neck syndrome, and posterior pelvic tilt may occur.

In fact, according to Health Insurance Review and Assessment Service in South Korea, the number of patients treated for turtle neck syndrome was confirmed to have increased by about 16.4% from 2,050,633 in 2017 to 2,387,401 in 2021. Since problems due to slouched postures may cause diseases from muscle fatigue and migraines to herniated discs, spinal deformation, and subsequent changes in lung function, it is important to maintain correct posture for a healthy life.

In this regard, technologies for dealing with the aforementioned problems are disclosed, including: technology for classifying postures by calculating angles of a spine and a face through image analysis; technology for classifying postures by using values measured from sensors worn on a user's body; and technology for classifying postures according to distances between a monitor and the user's face.

In the conventional technologies, there are problems in that the technology for classifying the postures through the image analysis is complex in terms of calculations and the technology for classifying the postures by using the body-worn sensors causes inconvenience as the sensors are attached to the user's body, thereby interfering with work. In addition, the conventional technology for classifying the postures according to the distances from the user's face has limitations in that the postures could not be subdivided and classified in detail and error notifications could not be provided depending on changes in the user's postures.

DISCLOSURE

Technical Problem

An objective of the present disclosure is to solve the above problems, and to provide a sitting posture determination device and method capable of determining sitting postures subdivided according to distances from a user, the distances being measured by distance sensors respectively installed at top and bottom portions of a monitor.

The objective of the present disclosure is not limited to the objective mentioned above, and other objectives not mentioned herein will be clearly understood from the following description.

Technical Solution

According to one aspect of the present disclosure to achieve the above-described objective, there is provided a sitting posture determination device, including: a measurement data generation unit configured to generate measurement data composed of a plurality of top portion measurement values and a plurality of bottom portion measurement values for a plurality of time points over time by receiving input of the top portion measurement portion measurement values respectively input from an top portion distance sensor and bottom portion distance sensor, which are respectively installed at top and bottom portions of a monitor and for measuring distances from a user; a correct posture determination unit configured to output a time point-specific top portion measurement value and bottom portion measurement value, which are out of a range preset for correct posture, by extracting the top portion measurement value and bottom portion measurement value at each time point in chronological order from the measurement data and comparing the top portion measurement value and bottom portion measurement value extracted at each time point with the range preset for the correct posture; and a posture classification unit configured to select and output any one of a plurality of classification values corresponding to a plurality of postures preset according to the time point-specific top portion measurement value and bottom portion measurement value which are output from the posture determination unit.

According to another aspect of the present disclosure, there is provided a sitting posture determination method performed by a sitting posture determination device, the sitting posture determination method including: generating measurement data composed of a plurality of top portion measurement values and a plurality of bottom portion measurement values for a plurality of time points over time by receiving input of the top portion measurement values and bottom portion measurement values respectively input from a top portion distance sensor and bottom portion distance sensor, which are respectively installed at top and bottom portions of a monitor and for measuring distances from a user; outputting a time point-specific top portion measurement value and bottom portion measurement value, which are out of a range preset for correct posture, by extracting the top portion measurement value and bottom portion measurement value at each time point in chronological order from the measurement data and comparing the top portion measurement value and bottom portion measurement value at each time point with the range preset for the correct posture; and selecting and outputting any one of a plurality of classification values corresponding to a plurality of postures preset according to the time point-specific top portion measurement value and bottom portion measurement value which are output from the outputting of the top portion measurement value and bottom portion measurement value at each time point and out of the range preset for the correct posture.

Advantageous Effects

According to the present disclosure, there is an effect of providing a sitting posture determination device and method capable of determining sitting postures subdivided according to distances from a user, the distances being measured by distance sensors respectively installed at top and bottom portions of a monitor.

The sitting posture determination device and method according to the present disclosure has another effect of helping a user maintain a correct posture by providing notifications according to posture determination results.

In addition, the sitting posture determination device and method according to the present disclosure may expect to have a yet another effect of maximally reducing error alarms by using a plurality of consecutive measurement values in chronological order to classify postures.

The effects of the present disclosure are not limited to the above-mentioned effects, and other effects not mentioned herein will be clearly understood by those skilled in the art from the description in the claims.

BEST MODE

Figure 1:
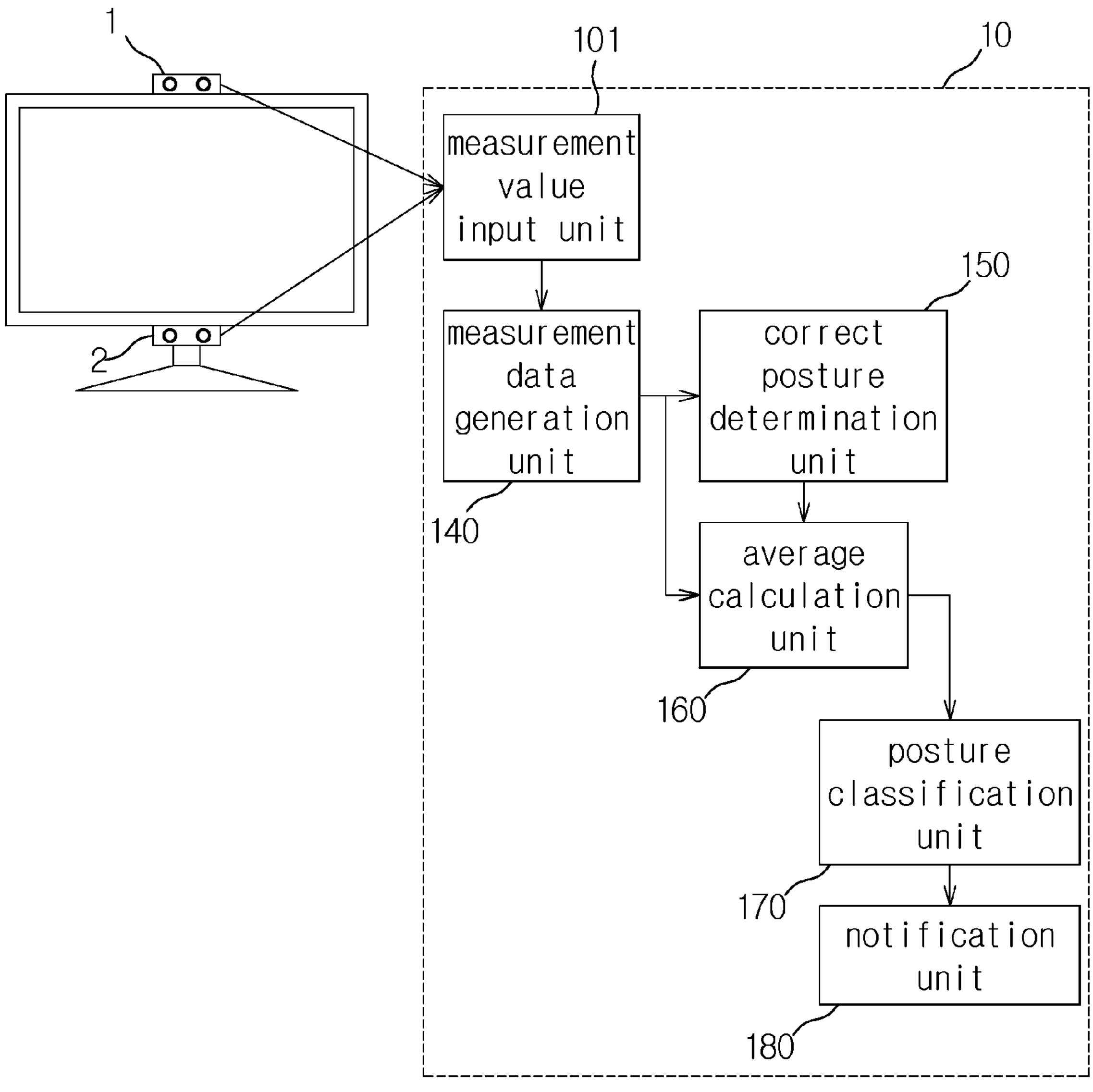
FIG. 1 is a block diagram illustrating a sitting posture determination device according to an exemplary embodiment of the present disclosure.

According to one aspect of the present disclosure to achieve the above-described objective, there is provided a sitting posture determination device, including: a measurement data generation unit configured to generate measurement data composed of a plurality of top portion measurement values and a plurality of bottom portion measurement values for a plurality of time points over time by receiving input of the top portion measurement values and bottom portion measurement values respectively input from an top portion distance sensor and bottom portion distance sensor, which are respectively installed at top and bottom portions of a monitor and for measuring distances from a user; a correct posture determination unit configured to output a time point-specific top portion measurement value and bottom portion measurement value, which are out of a range preset for correct posture, by extracting the top portion measurement value and bottom portion measurement value at each time point in chronological order from the measurement data and comparing the top portion measurement value and bottom portion measurement value extracted at each time point with the range preset for the correct posture; and a posture classification unit configured to select and output any one of a plurality of classification values corresponding to a plurality of postures preset according to the time point-specific top portion measurement value and bottom portion measurement value which are output from the posture determination unit.

The correct posture determination unit may extract a top portion measurement value and bottom portion measurement value at each time point from an earliest measurement time point in chronological order from the measurement data to determine whether the measurement values exceed the range preset for the correct posture, and may output the top portion measurement value and bottom portion measurement value at each of the plurality of time points when the top portion measurement value and bottom portion measurement value at each of the plurality of time points consecutively exceed the range preset for the correct posture as many times as a preset count.

In this case, the sitting posture determination device may further include an average calculation unit for calculating a top portion average value and a bottom portion average value by separately averaging the top portion measurement values and bottom portion measurement values over each of the plurality of time points, the top portion measurement values and bottom portion measurement values being output from the correct posture determination unit, wherein the posture classification unit may select and output any one of a plurality of classification values corresponding to a plurality of preset postures based on whether the top portion average value and bottom portion average value are included in a plurality of ranges preset corresponding to a plurality of postures.

In addition, the sitting posture determination device may further include a notification unit for providing notifications through preset notification means according to classification values output from the posture classification unit.

According to another aspect of the present disclosure, there is provided a sitting posture determination method performed by a sitting posture determination device, the sitting posture determination method including: generating measurement data composed of a plurality of top portion measurement values and a plurality of bottom portion measurement values for a plurality of time points over time by receiving input of the top portion measurement values and bottom portion measurement values respectively input from an top portion distance sensor and bottom portion distance sensor, which are respectively installed at top and bottom portions of a monitor and for measuring distances from a user; outputting a time point-specific top portion measurement value and bottom portion measurement value, which are out of a range preset for correct posture, by extracting the top portion measurement value and bottom portion measurement value at each time point in chronological order from the measurement data and comparing the top portion measurement value and bottom portion measurement value at each time point with the range preset for the correct posture; and selecting and outputting any one of a plurality of classification values corresponding to a plurality of postures preset according to the time point-specific top portion measurement value and bottom portion measurement value which are output from the outputting of the top portion measurement value and bottom portion measurement value at each time point and out of the range preset for the correct posture.

The outputting of the time point-specific top portion measurement value and bottom portion measurement value which are out of the range preset for the correct posture extracts the top portion measurement value and bottom portion measurement value at each time point from an earliest measurement time point in the chronological order from the measurement data so as to determine whether the top and bottom portion measurement values exceed the range preset for the correct posture, and determines whether the top portion measurement value and bottom portion measurement value at each of the plurality of time points consecutively exceed the range preset for the correct posture as many times as a preset count so as to output the top portion measurement value and bottom portion measurement value at each of the plurality of time points when the top portion measurement value and bottom portion measurement value at each of the plurality of time points consecutively exceed the range preset for the correct posture as many times as the preset count.

Here, the selecting and outputting of any one of the plurality of classification values corresponding to the plurality of preset postures includes: calculating a top portion average value and a bottom portion average value by separately averaging the top portion measurement values and bottom portion measurement values over each of the plurality of time points, the top portion measurement values and bottom portion measurement values being output from the outputting of the top portion measurement value and bottom portion measurement value at each time point and out of the range preset for the correct posture; and selecting and outputting any one of the plurality of classification values corresponding to the plurality of postures preset according to whether the top portion average value and bottom portion average value are comprised in a plurality of ranges preset corresponding to the plurality of postures.

In addition, the sitting posture determination method may further include providing notifications through preset notification means according to classification values output from the selecting and outputting of any one of the plurality of classification values corresponding to the plurality of preset postures, after the selecting and outputting of any one of the plurality of classification values corresponding to the plurality of preset postures.

Mode for Invention

Advantages and features of the present disclosure, and methods of achieving them will become apparent with reference to the exemplary embodiments described below in detail together with the accompanying drawings. However, the present disclosure is not limited to the exemplary embodiments disclosed below, but will be implemented in various different forms. Rather, these exemplary embodiments are provided so that the disclosure of the present disclosure will be thorough and complete, and will fully convey the concept of the present disclosure to those skilled in the art, and the present disclosure will only be defined by the descriptions of the appended claims. Meanwhile, the terminology used herein is for the purpose of describing the exemplary embodiments only and is not intended to be limiting of the present disclosure. In the present specification, the singular form also includes the plural form unless otherwise specified in the phrase.

Figure 2:
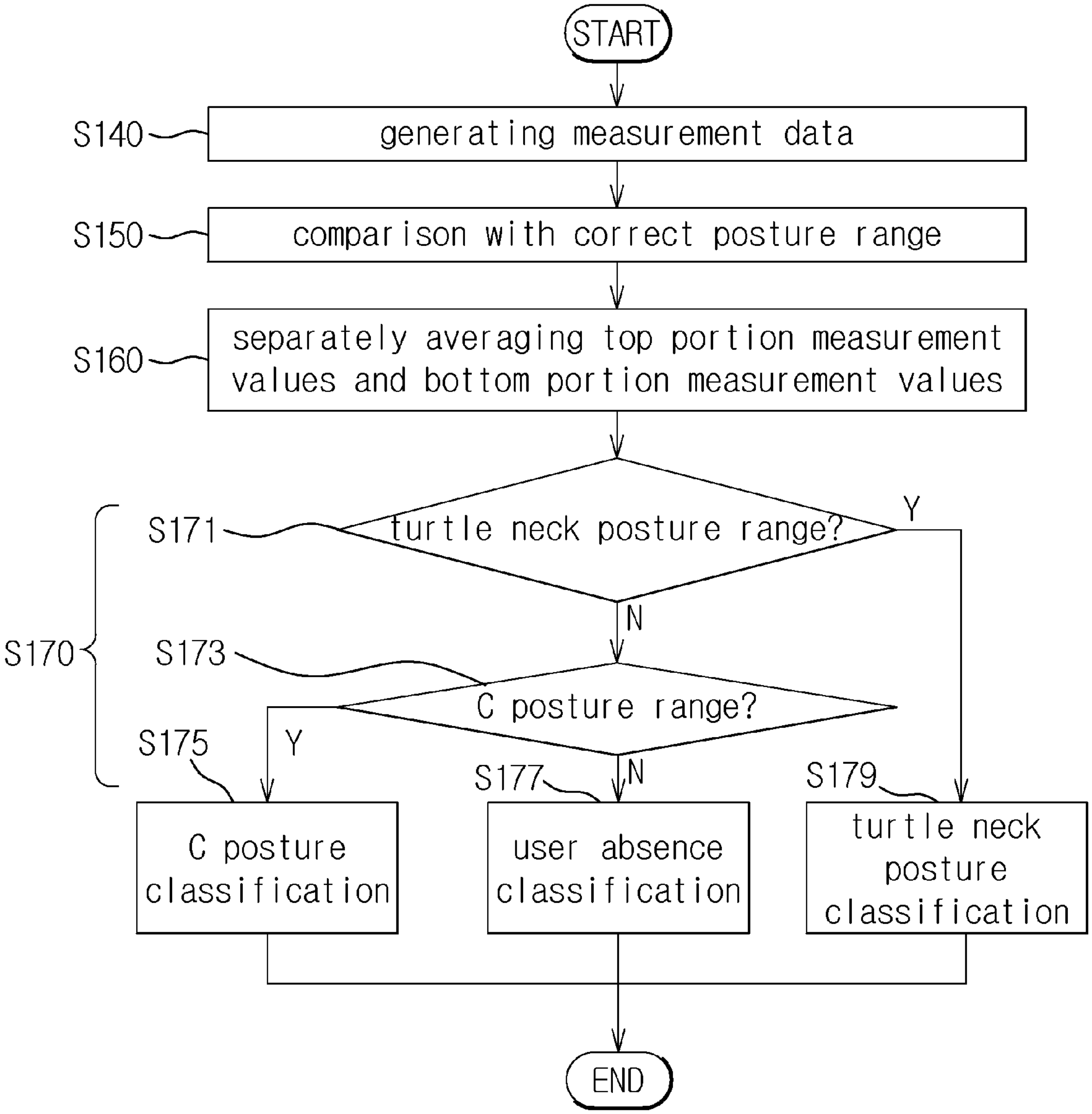
FIG. 2 is a flowchart illustrating a sitting posture determination method according to another exemplary embodiment of the present disclosure.

FIG. 1 is a block diagram illustrating a sitting posture determination device according to an exemplary embodiment of the present disclosure, and FIG. 2 is a flowchart illustrating a sitting posture determination method according to another exemplary embodiment of the present disclosure.

The sitting posture determination method according to another exemplary embodiment of the present disclosure may be performed by the sitting posture determination device 10 according to the exemplary embodiment of the present disclosure.

Hereinafter, for convenience of description, same reference numerals will be matched to identical components and redundant description thereof will be omitted.

The sitting posture determination device 10 may include a measurement value input unit 101, a measurement data generation unit 140, a correct posture determination unit 150, an average calculation unit 160, a posture classification unit 170, and a notification unit 180.

The measurement value input unit 101 may receive input of a top portion measurement value and a bottom portion measurement value respectively from a top portion distance sensor 1 and a bottom portion distance sensor 2, which are respectively installed at a top portion and a bottom portion of a monitor to measure distances from a user.

In step S140, the measurement data generation unit 140 may respectively receive input of the top portion measurement value and bottom portion measurement value input from the top portion distance sensor 1 and bottom portion distance sensor 2, which measure the distances from the user and are installed at the top portion and the bottom portion of the monitor, and generate measurement data composed of a plurality of top portion measurement values and a plurality of bottom portion measurement values at a plurality of time points over time.

In step S140, the measurement data generation unit 140 may receive input of the top portion measurement values and bottom portion measurement values input from the measurement value input unit 101 for a predetermined time period, and generate the measurement data composed of the plurality of top portion measurement values and the plurality of bottom portion measurement values at the plurality of time points over time.

In step S150, the correct posture determination unit 150 may extract a top portion measurement value and bottom portion measurement value at each time point in chronological order from the measurement data generated by the measurement data generation unit 140, compare the top portion measurement value and bottom portion measurement value extracted at each time point with a range preset for correct posture, and output a time point-specific top portion measurement value and bottom portion measurement value which are out of the range preset for the correct posture.

For example, the range for the correct posture may be preset to be from 50 or more to less than 70 for a top portion measurement value and from 50 or more to less than 70 for a bottom portion measurement value.

In step S150, the correct posture determination unit 150 may extract a top portion measurement value and bottom portion measurement value at each time point from an earliest measurement time point in chronological order from the measurement data to determine whether the measurement values exceed the range preset for the correct posture, and may output the top portion measurement value and bottom portion measurement value at each of the plurality of time points when the top portion measurement value and bottom portion measurement value at each of the plurality of time points consecutively exceed the range preset for the correct posture as many times as a preset count.

Figure 3:
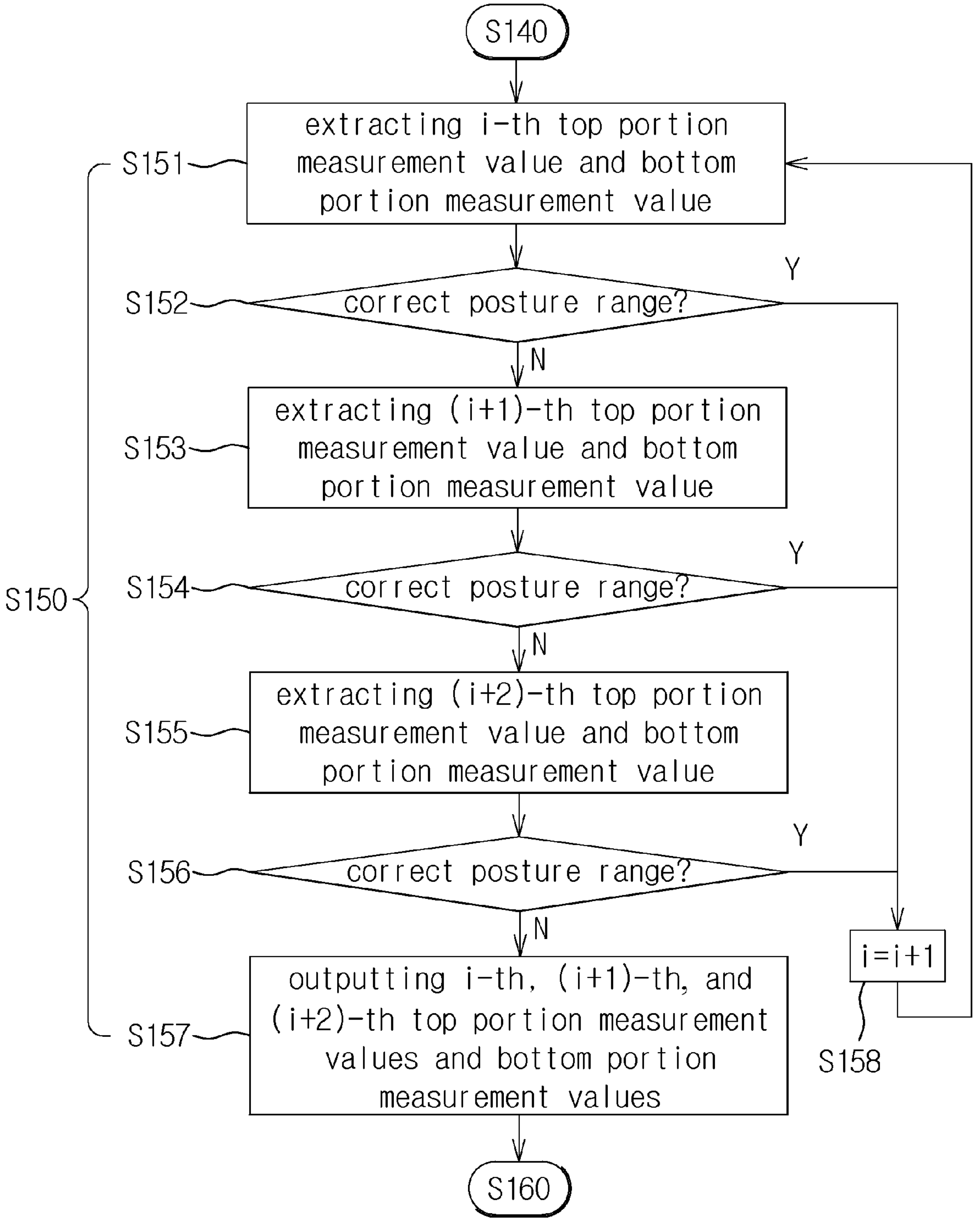
FIG. 3 is a detailed flowchart for comparing measurement values with a correct posture range in the exemplary embodiments of the present disclosure.

Referring to FIG. 3, the correct posture determination unit 150 may extract the top portion measurement value and bottom portion measurement value at each time point from the earliest measurement time point in chronological order from the measurement data in step S151, determine whether the extracted top portion measurement value and bottom portion measurement value exceed the range preset for the correct posture in step S152, and increase the number of time points for serving as a reference to extract top portion measurement values and bottom portion measurement values in step S158 (e.g., i=i+1) when the measurement values do not exceed the range preset for the correct posture, subsequently routing the process back to step S151 for the next consecutive time point.

The correct posture determination unit 150 extracts a top portion measurement value and bottom portion measurement value of a second time point, which is the next time point after a first time point, when the top portion measurement value and bottom portion measurement value at the first time point exceed the range preset for the correct posture in step S153, and determine whether the top portion measurement value and bottom portion measurement value at the second time point exceed the range preset for the correct posture in step S154. If the measurement values at the second time point do not exceed the range preset for the correct posture, the process loops back via step S158 to increment the reference index and return to step S151.

In addition, the correct posture determination unit 150 may extract a top portion measurement value and bottom portion measurement value of a third time point, which is the next time point after the second time point, when the top portion measurement value and bottom portion measurement value at the second time point exceed the range preset for the correct posture in step S155, determine whether the top portion measurement value and bottom portion measurement value at the third time point exceed the range preset for the correct posture in step S156, and output the top portion measurement value and bottom portion measurement value at each of the first to third time points when the top portion measurement value and bottom portion measurement value at the third time point exceed the range preset for the correct posture in step S157.

Figure 4:
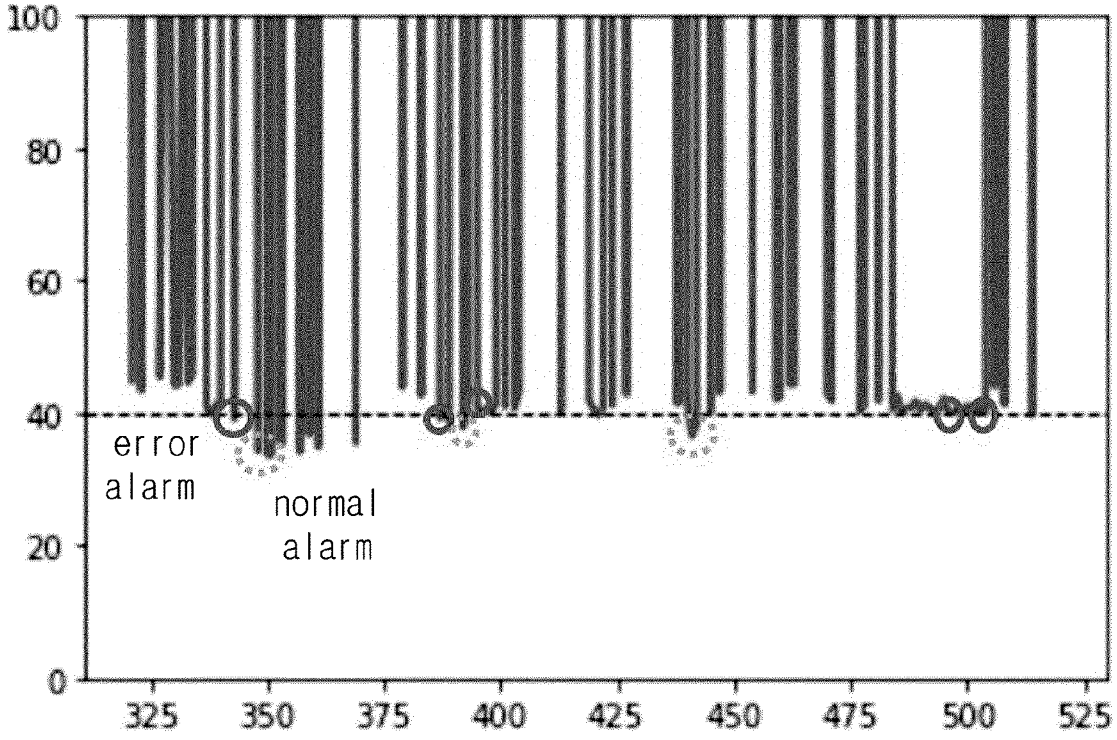
FIG. 4 is an exemplary view illustrating time points of providing alarms when determination is performed on the basis of a simple threshold value in first measurement data obtained by measuring distances from a user.
Figure 5:
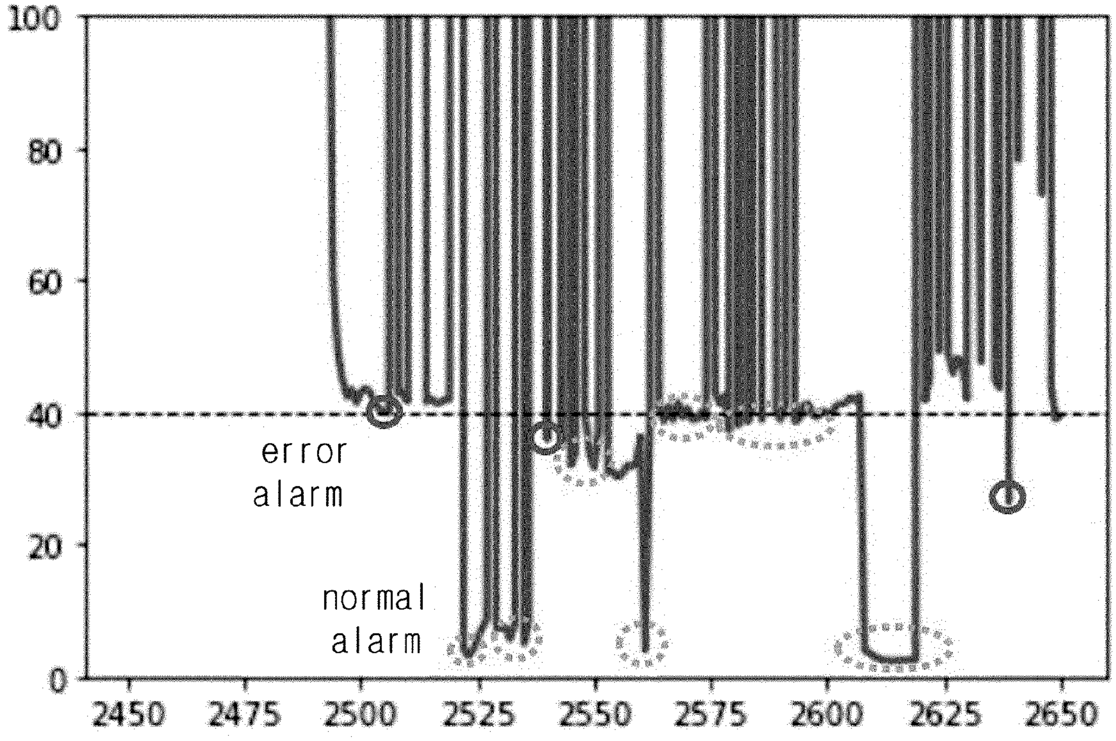
FIG. 5 is an exemplary view illustrating time points of providing alarms when determination is performed on the basis of a simple threshold value in second measurement data obtained by measuring distances from the user.

Referring to FIGS. 4 and 5, it may be confirmed that in a case of providing alarms according to whether distance measurement values measured over time have simply exceeded a threshold value at each time point, error alarms (i.e., false alarms) are generated even when the threshold value is temporarily exceeded in addition to normal alarms.

Accordingly, the correct posture determination unit 150 determines whether the top portion measurement values and bottom portion measurement values exceed the range preset for the correct posture at the plurality of consecutive time points.

Accordingly, errors generated when postures are classified on the basis of the measurement values that momentarily deviate from the correct posture due to a user's movement or environmental changes may be eliminated.

That is, the correct posture determination unit 150 continually outputs measurement values that deviate from the correct posture and uses the measurement values for sitting posture classification, whereby the accuracy of the posture classification may be increased.

In step S160, the average calculation unit 160 may calculate both of a top portion average value which is an average of a plurality of top portion measurement values, and a bottom portion average value which is an average of a plurality of bottom portion measurement values by separately averaging the plurality of top portion measurement values and bottom portion measurement values, which are output from the correct posture determination unit 150. bottom portion average value which is an average of a plurality of bottom portion measurement values by separately averaging the plurality of top portion measurement values and bottom portion measurement values, which are output from the correct posture determination unit 150.

In step S170, the posture classification unit 170 may select and output any one of a plurality of classification values corresponding to a plurality of postures preset according to the top portion measurement value and bottom portion measurement value at each time point output from the posture determination unit 150.

In step S170, the posture classification unit 170 may select and output any one of the plurality of classification values corresponding to the plurality of postures preset according to whether the top portion average value and bottom portion average value which are calculated by the average calculation unit 160 are included in a plurality of ranges preset corresponding to the plurality of postures.

The posture classification unit 170 may determine whether a top portion average value and bottom portion average value are included within a range preset for turtle neck posture in step S171, and output a preset classification value for a turtle neck posture when the top portion average value and bottom portion average value are included within the range preset for the turtle neck posture in step S179.

For example, a range for the turtle neck posture may be preset to be less than 50 for an top portion average value and to be less than 55 for a bottom portion average value.

The posture classification unit 170 may determine whether an top portion average value and bottom portion average value are within a range preset for C posture when the top portion average value and bottom portion average value are not included within the range preset for the turtle neck posture in step 173, and output a preset classification value for the C posture when the top portion average value and bottom portion average value are included within the range preset for the C posture in step 175.

Here, the range for the C posture may be preset to be from greater than or equal to 75 to less than or equal to 125 for an top portion average value and to be from greater than or equal to 70 to less than or equal to 100 for a bottom portion average value.

The posture classification unit 170 may output a preset classification value for user absence when a top portion average value and bottom portion average value are not included in the range preset for the C posture.

According to the above-described configuration, subdivided classification of a user's sitting posture is achievable.

The notification unit 180 may provide notifications through preset notification means according to classification values output from the posture classification unit 170.

The notification means may be provided with LEDs so as to provide a notification by emitting LED light according to a classification value output from the posture classification unit 170, may be provided with a speaker so as to provide a notification by outputting a preset voice through the speaker according to a classification value output from the posture classification unit 170, and may be provided with a vibration unit so as to provide a notification by generating vibration from the vibration unit according to a classification value output from the posture classification unit 170.

The notification means may be applied to a smartphone owned by a user to provide a notification by transmitting a preset message according to a classification value output from the posture classification unit 170.

Figure 6:
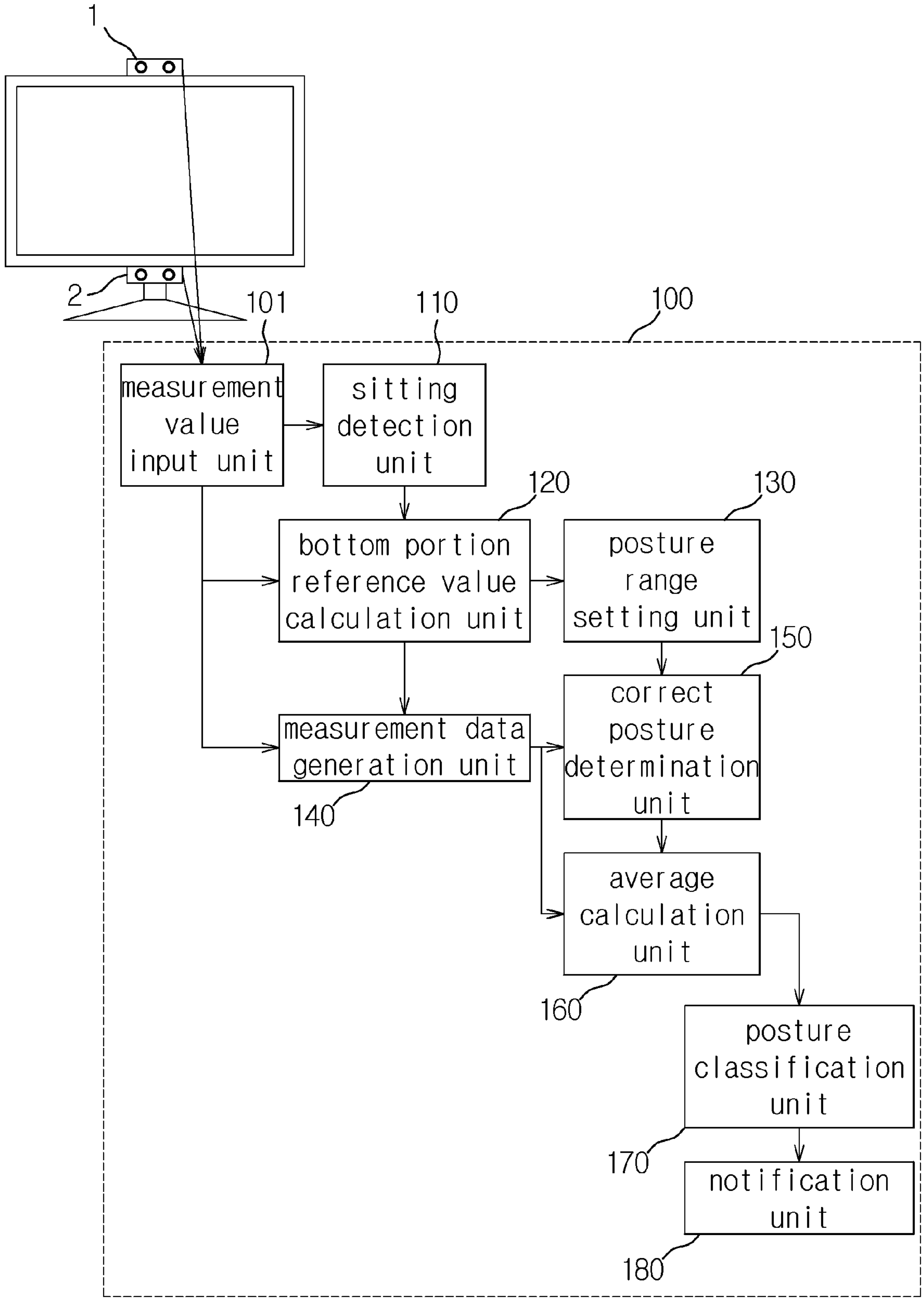
FIG. 6 is a block diagram illustrating a sitting posture determination device according to a yet another exemplary embodiment of the present disclosure.
Figure 7:
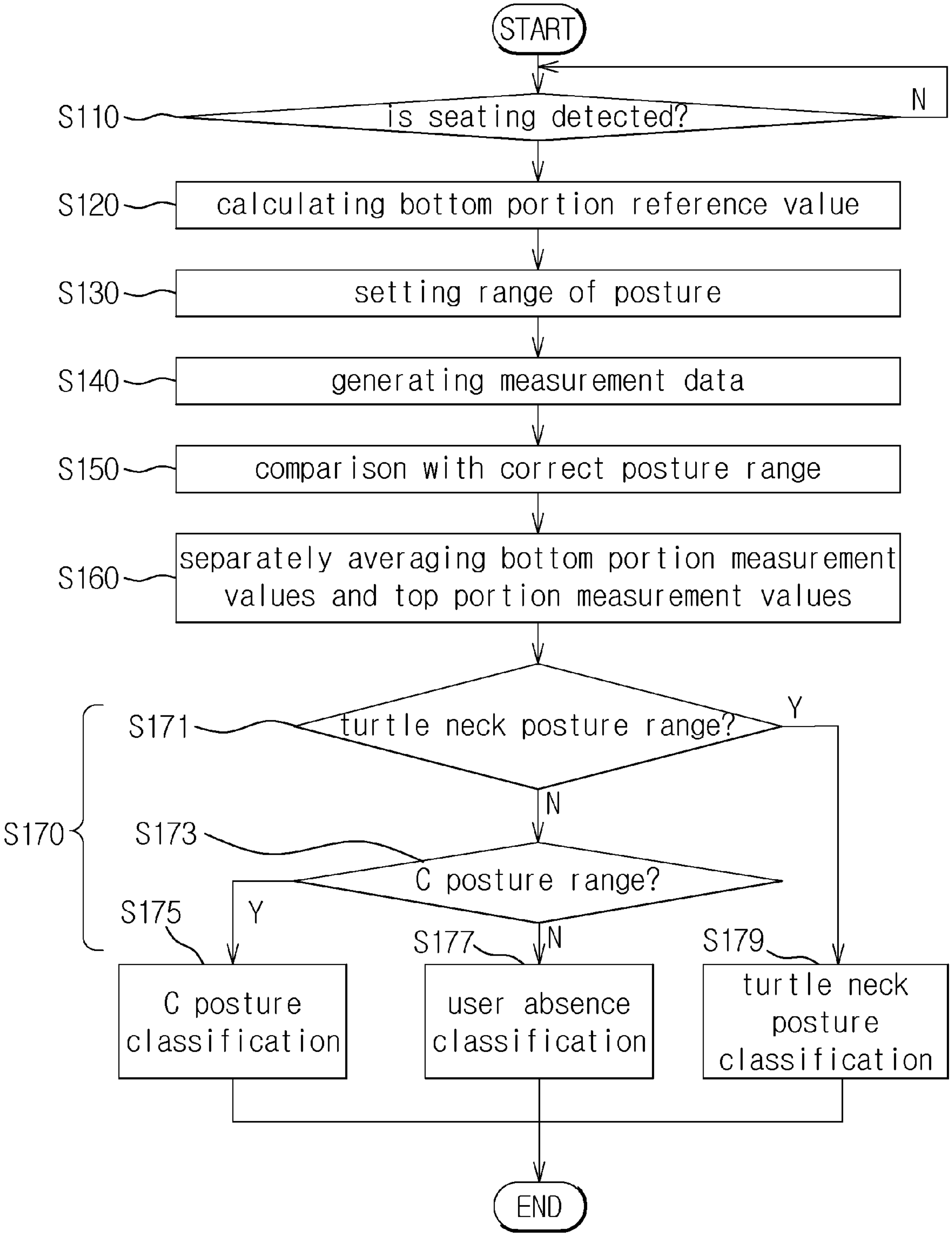
FIG. 7 is a flowchart illustrating a sitting posture determination method according to a still another exemplary embodiment of the present disclosure.

FIG. 6 is a block diagram illustrating a sitting posture determination device according to a yet another exemplary embodiment of the present disclosure, and FIG. 7 is a flowchart illustrating a sitting posture determination method according to a still another exemplary embodiment of the present disclosure.

The sitting posture determination method according to the still another exemplary embodiment of the present disclosure may be performed by the sitting posture determination device 100 according to the yet another exemplary embodiment of the present disclosure.

The sitting posture determination device 100 according to the yet another exemplary embodiment of the present disclosure may further include a sitting detection unit 110, a bottom portion reference value calculation unit 120, and a posture range setting unit 130.

Hereinafter, in the block diagram of FIG. 6, the same reference numerals will be matched to the same components as those of FIG. 1, and detailed descriptions thereof will be omitted. In addition, for convenience of description, the same reference numerals will be matched to the components of FIGS. 2 and 7 that match the components of the previously described drawings, and detailed description thereof will be omitted.

Referring to FIG. 6, the sitting posture determination device 100 may include a measurement value input unit 101, a sitting detection unit 110, a bottom portion reference value calculation unit 120, a posture range setting unit 130, a measurement data generation unit 140, a correct posture determination unit 150, an average calculation unit 160, a posture classification unit 170, and a notification unit 180.

The measurement value input unit 101 may be installed at each of top and bottom portions of a monitor, so as to respectively receive input of a top portion measurement value and bottom portion measurement value from a top portion distance sensor and a bottom portion distance sensor, which measure distances from a user.

In step S110, the seating detection unit 110 may detect seating according to whether a top portion measurement value and a bottom portion measurement value, which are input from the measurement value input unit 101, are within preset threshold values.

The sitting detection unit 110 may determine that a user is seated when a top portion measurement value and a bottom portion measurement value, which are input from the measurement value input unit 101, are within preset threshold values, and may repeat the sitting detection for a top portion measurement value and a bottom portion measurement value, which are input from the measurement value input unit 101 at the next time point when the top portion measurement value and bottom portion measurement value, which are input from the measurement value input unit 101, are out of the preset threshold value.

In step S120, the bottom portion reference value calculation unit 120 may receive input of top portion measurement values and bottom portion measurement values, which are input from the measurement value input unit 101 for a preset time period from a time point when the sitting detection unit 110 determines that a person is seated, so as to average the bottom portion measurement values respectively obtained by a plurality of time points, thereby calculating a bottom portion reference value.

In step S120, the bottom portion reference value calculation unit 120 may receive input of top portion measurement values and bottom portion measurement values, which are input from the measurement value input unit 101 for a preset time period from a time when the sitting detection unit 110 determines that the person is seated, and may remove, among the bottom portion measurement values over each of the plurality of time points, an outlier of a bottom portion reference value whose difference from a top portion measurement value at each time point exceeds a preset tolerance value, so as to average the bottom portion measurement values over each of the plurality of time points and from which each outlier is removed, thereby calculating a bottom portion reference value.

According to the above-described configuration, when an obstacle such as a tumbler is placed between a monitor and a user and a bottom portion measurement value based on a distance between the monitor and the obstacle is input, the bottom portion reference value calculation unit 120 may remove this bottom portion measurement value as an outlier.

Accordingly, by calculating highly reliable bottom portion reference values and setting a posture determination range based on these bottom portion reference values, the posture of each user may be accurately determined.

In step S130, the posture range setting unit 130 may set respective ranges of a top portion measurement value and bottom portion measurement value for each of the plurality of postures on the basis of the bottom portion reference values calculated by the bottom portion reference value calculation unit 120.

In step S130, the posture range setting unit 130 may set as a first reference value a value obtained by subtracting a preset first range value (e.g., 10) from a bottom portion reference value, may set as a second reference value a value obtained by adding the preset first range value (e.g., 10) to the bottom portion reference value, may set as a third reference value a value obtained by adding a preset second range value (e.g., 60) to the bottom portion reference value, may set as a range for the correct posture a top portion measurement value and bottom portion measurement value each greater than or equal to the first reference value and less than the second reference value, may set as a range for the turtle neck posture a top portion measurement value less than the first reference value and a bottom portion measurement value less than the second reference value, and may set as a range for the C posture a top portion measurement value greater than or equal to the second reference value but less than the third reference value and a bottom portion measurement value greater than or equal to the second reference value but less than the third reference value.

In step S140, the measurement data generation unit 140 may receive a top portion measurement value and bottom portion measurement value at each of a plurality of time points for a preset time periods after a time point when the bottom portion reference value is calculated by the bottom portion reference value calculation unit 120, and then generate measurement data composed of a plurality of top portion measurement values and a plurality of bottom portion measurement values at the plurality of time points over time.

In step S150, the correct posture determination unit 150 may extract an top portion measurement value and bottom portion measurement value at each time point in chronological order from the measurement data generated by the measurement data generation unit 140, compare the top portion measurement value and bottom portion measurement value extracted at each time point with a range preset for correct posture, and output a time point-specific top portion measurement value and bottom portion measurement value which are out of the range preset for the correct posture.

In addition, the average calculation unit 160 may calculate a top portion average value and a bottom portion average value by separately averaging a plurality of top portion measurement values and bottom portion measurement values, which are output from the correct posture determination unit 150 in step S160, and the posture classification unit 170 may select and output any one of a plurality of classification values corresponding to the plurality of preset postures based on the top portion average value and bottom portion average value in step S170.

Meanwhile, the blocks in the attached block diagram and the steps in the flowchart may be implemented as computer instructions performing designated functions while loaded on a processor or memory of an electronic device (e.g., a general-purpose computer, a special-purpose computer, a portable laptop computer, and a network computer) capable of data processing. Since these computer program instructions may be stored in a computer-readable memory, functions described in blocks of a block diagram or steps of a flowchart may also be produced as a product including an instruction method for performing the functions.

It will be understood that those skilled in the art to which the present disclosure pertains may implement the present disclosure in other specific forms without departing from the technical spirit or essential features thereof. Therefore, it should be understood that the above-described exemplary embodiments are illustrative in all respects and not restrictive. The scope of the present disclosure is indicated by the following claims rather than the above detailed description, and all changes or modifications derived from the meaning and scope of the claims and equivalent concepts should be interpreted as being included in the claims of the present disclosure.

INDUSTRIAL APPLICABILITY

The present disclosure relates to a sitting posture determination device and method capable of determining a sitting posture according to distances between a monitor and a user, the distances being measured by using distance sensors.

The invention claimed is:

1. A sitting posture determination device, comprising:

a measurement value input unit configured to receive a plurality of top portion measurement values and a plurality of bottom portion measurement values respectively from a top portion distance sensor and a bottom portion distance sensor, which are respectively installed at top and bottom portions of a monitor and for measuring distances from a user;

a measurement data generation processor configured to generate measurement data composed of the plurality of top portion measurement values and the plurality of bottom portion measurement values for a plurality of time points over time by receiving input of the top portion measurement values and bottom portion measurement values from the measurement value input unit;

a correct posture determination processor configured to output a time point-specific top portion measurement value and bottom portion measurement value, which are out of a range preset for correct posture, by extracting the top portion measurement value and bottom portion measurement value at each time point in chronological order from the measurement data and comparing the top portion measurement value and bottom portion measurement value extracted at each time point with the range preset for the correct posture; and a posture classification processor configured to select and output any one of a plurality of classification values corresponding to a plurality of postures preset according to the time point-specific top portion measurement value and bottom portion measurement value which are output from the correct posture determination processor, wherein the device further comprises a notification unit configured to provide a notification through a preset notification means according to the selected and output classification value, and wherein the selected and output classification value comprises a turtle neck posture classification value, a C posture classification value, or a user absence classification value.

2. The sitting posture determination device of claim 1, wherein the correct posture determination processor extracts the top portion measurement value and bottom portion measurement value at each time point from an earliest measurement time point in chronological order from the measurement data to determine whether the top and bottom portion measurement values exceed the range preset for the correct posture, and outputs the top portion measurement value and bottom portion measurement value at each of the plurality of time points when the top portion measurement value and bottom portion measurement value at each of the plurality of time points consecutively exceed the range preset for the correct posture as many times as a preset count.

3. The sitting posture determination device of claim 2, further comprising:

an average calculation processor for calculating a top portion average value and a bottom portion average value by separately averaging the top portion measurement values and bottom portion measurement values over each of the plurality of time points, the top portion measurement values and bottom portion measurement values being output from the correct posture determination processor, wherein the posture classification processor selects and outputs any one of the plurality of classification values corresponding to the plurality of postures preset according to whether the top portion average value and the bottom portion average value are comprised in a plurality of ranges preset corresponding to the plurality of postures.

4. A sitting posture determination method performed by a sitting posture determination device, the sitting posture determination method comprising:

receiving, by a measurement value input unit, a plurality of top portion measurement values and a plurality of bottom portion measurement values respectively from a top portion distance sensor and a bottom portion distance sensor, which are respectively installed at top and bottom portions of a monitor and for measuring distances from a user;

generating, by a measurement data generation processor, measurement data composed of the plurality of top portion measurement values and the plurality of bottom portion measurement values for a plurality of time points over time by receiving input of the top portion measurement values and bottom portion measurement values from the measurement value input unit;

outputting, by a correct posture determination processor, a time point-specific top portion measurement value and bottom portion measurement value, which are out of a range preset for correct posture, by extracting the top portion measurement value and bottom portion measurement value at each time point in chronological order from the measurement data and comparing the top portion measurement value and bottom portion measurement value at each time point with the range preset for the correct posture; and selecting and outputting, by a posture classification processor, any one of a plurality of classification values corresponding to a plurality of postures preset according to the time point-specific top portion measurement value and bottom portion measurement value which are output from the outputting of the top portion measurement value and bottom portion measurement value at each time point and out of the range preset for the correct posture, wherein the selected and output classification value comprises a turtle neck posture classification value, a C posture classification value, or a user absence classification value; and providing, by a notification unit, a notification through a preset notification means according to the selected and output classification value.

5. The sitting posture determination method of claim 4, wherein the outputting of the time point-specific top portion measurement value and bottom portion measurement value which are out of the range preset for the correct posture extracts the top portion measurement value and bottom portion measurement value at each time point from an earliest measurement time point in chronological order from the measurement data so as to determine whether the top and bottom portion measurement values exceed the range preset for the correct posture, and determines whether the top portion measurement value and bottom portion measurement value at each of the plurality of time points consecutively exceed the range preset for the correct posture as many times as a preset count so as to output the top portion measurement value and bottom portion measurement value at each of the plurality of time points when the top portion measurement value and bottom portion measurement value at each of the plurality of time points consecutively exceed the range preset for the correct posture as many times as the preset count.

6. The sitting posture determination method of claim 5, wherein the selecting and outputting of any one of the plurality of classification values corresponding to the plurality of preset postures comprises:

calculating a top portion average value and a bottom portion average value by separately averaging the top portion measurement values and bottom portion measurement values over each of the plurality of time points, the top portion measurement values and bottom portion measurement values being output from the outputting of the top portion measurement value and bottom portion measurement value at each time point and out of the range preset for the correct posture; and selecting and outputting any one of the plurality of classification values corresponding to the plurality of postures preset according to whether the top portion average value and bottom portion average value are comprised in a plurality of ranges preset corresponding to the plurality of postures.

7. The sitting posture determination method of claim 4, wherein the notification unit provides the notification by emitting LED light from an LED, outputting a voice through a speaker, generating vibration via a vibration unit, or transmitting a message to a smartphone owned by the user.

* * * * *